(12) United States Patent
Di Cecco

(10) Patent No.: US 7,347,865 B2
(45) Date of Patent: Mar. 25, 2008

(54) EAR DUCT CLEANING DEVICE

(76) Inventor: Corrado Di Cecco, Corso Italia 61, I-17027 Pietra Ligure (IT)

( * ) Notice: Subject to any disclaimer, the term of this patent is extended or adjusted under 35 U.S.C. 154(b) by 700 days.

(21) Appl. No.: 10/647,051

(22) Filed: Aug. 25, 2003

(65) Prior Publication Data

US 2004/0097997 A1 May 20, 2004

(30) Foreign Application Priority Data

Sep. 4, 2002 (IT) .......................... GE2002A0079

(51) Int. Cl.
*A61F 11/00* (2006.01)
(52) U.S. Cl. .................................................. 606/162
(58) Field of Classification Search ................ 606/161, 606/162, 192; 604/103.07, 103.05
See application file for complete search history.

(56) References Cited

U.S. PATENT DOCUMENTS 6,152,940 A  11/2000  Carter

2002/0128598 A1 * 9/2002 Nobles .................. 604/103.07

FOREIGN PATENT DOCUMENTS

DE  2 048 798  4/1972
FR  2 706 288  12/1994

OTHER PUBLICATIONS

Patent Abstracts of Japan; vol. 1996, No. 04, Apr. 30, 1996 & JP 7 313394 A (Shigeru Ichikawa), Dec. 5, 1995 abstract—& JP 07 313394 A (Shigeru Ichikawa) Dec. 5, 1995 figures.

* cited by examiner

*Primary Examiner*—Michael Thaler
(74) *Attorney, Agent, or Firm*—Stites & Harbison PLLC; Marvin Petry

(57) ABSTRACT

Ear duct cleaning device, comprising a flexible tubular member, equipped at one end with an inflatable element and at its opposite end with means of supplying a fluid at a certain pressure, wherein said inflatable element, being coupled to means of controlling the inflation so that said inflatable element assumes, once inflated, a shape such that its radial extension with respect to the axis of said tubular element is considerably greater than that along the same axis.

18 Claims, 4 Drawing Sheets

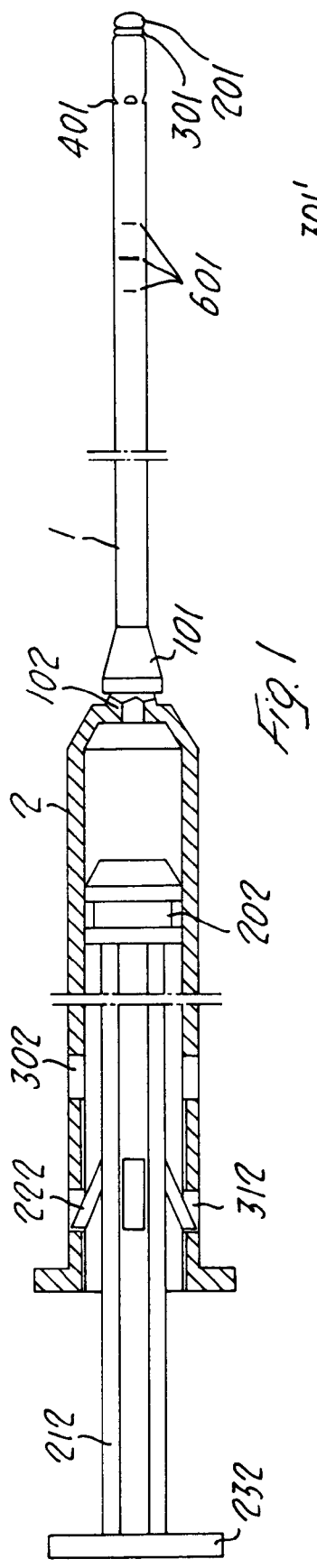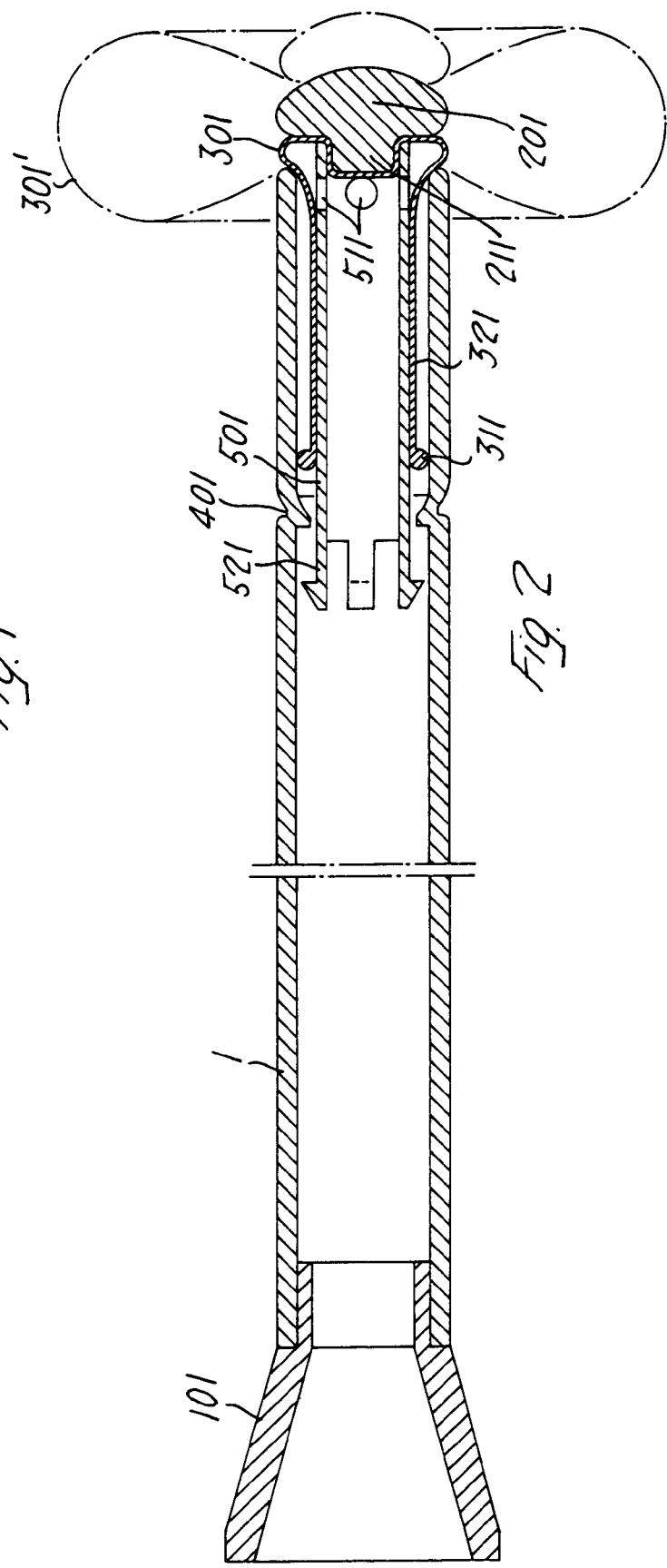

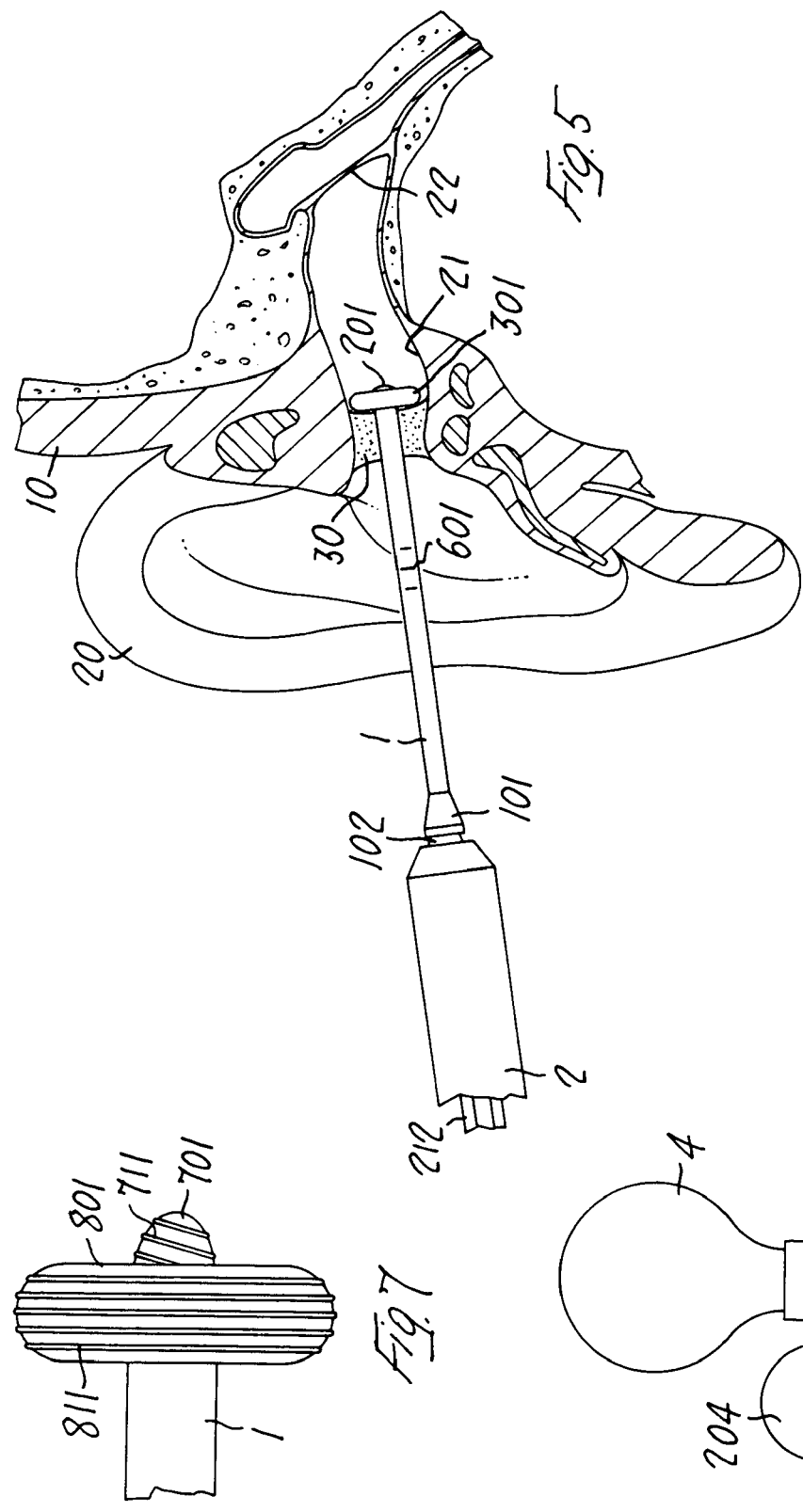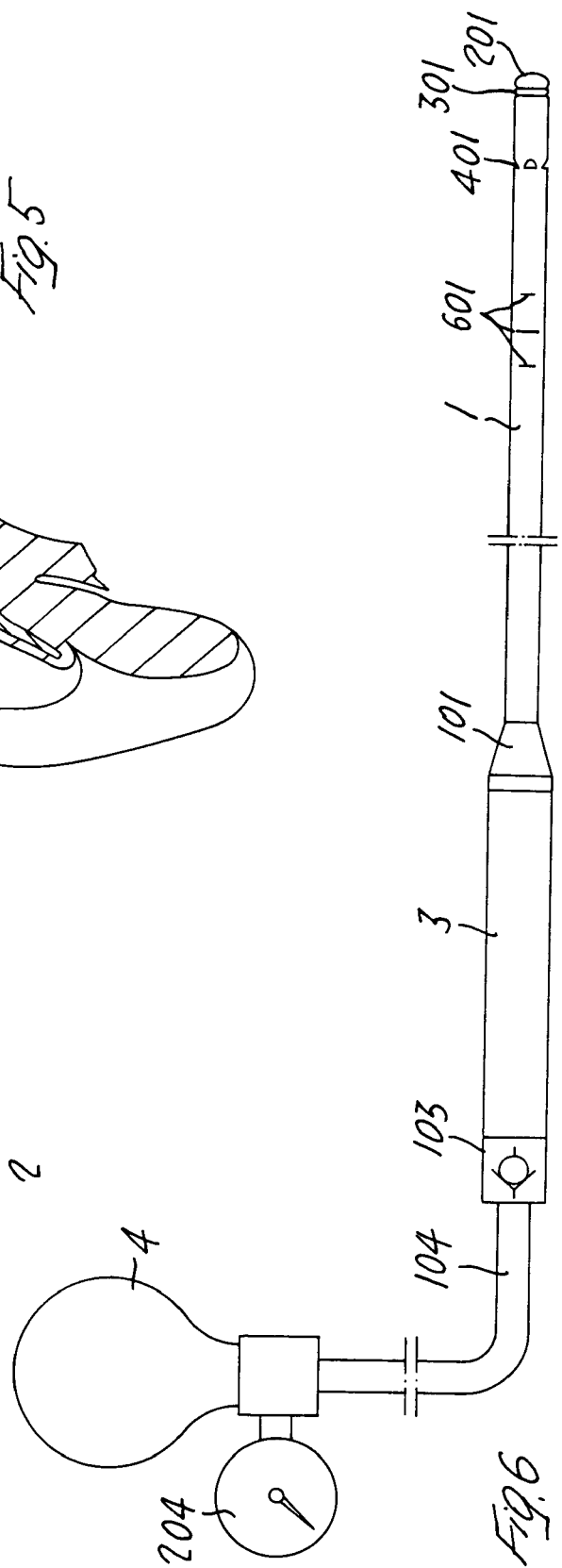

EAR DUCT CLEANING DEVICE

FIELD OF THE INVENTION

This invention relates to a device for cleaning the ear duct.

BACKGROUND OF THE INVENTION

The sebaceous secretion discharging into the ear duct can often induce accumulations such as to cause obstructions of the ear duct itself. In particular, the attempt to remove the accumulations by cottoned sticks, the so-called cotton flocks, may cause a greater compaction of the waxy substance, thus in fact inducing hearing disturbances of an even serious nature.

This type of problem generally calls for an expert's, a physician's or a nurse's attention capable of removing the occlusion, normally by utilising water jetted from a syringe or appropriate tools for inspecting the ear duct. Such interventions are usually complex in relation to the nature of the problem in itself, also rather painful and bothersome for the patient, and may result in an affection of the walls of the ear duct, which are easily irritated.

SUMMARY OF THE INVENTION

The purpose of this invention is to provide a device capable of performing an effective and as far as possible delicate cleaning of the ear duct in the presence, wholly or in part, of accumulations and obstructions of waxy material in the ear duct itself.

The object of this invention is therefore a device for cleaning the ear duct, comprising a flexible tubular member fitted at one end with an inflatable element, and at the other end with means of supplying a fluid at a certain pressure, where said inflatable element is coupled to inflation controlling means, capable of imparting to said inflatable element, once inflated, a shape such that its radial extension with respect to the axis of the said tubular member is considerably greater than along the same axis.

Said means for controlling the inflation of said inflatable element preferentially comprise means of limiting the extension of said inflatable element in the direction of the axis of said tubular member; said means may be composed of a tubular element over which said inflatable element is slipped, while sliding along lengthwise inside said tubular member, coaxially and concentrically with the same; the end pointed toward the outside of said member carries means for blocking said inflatable element, and the end pointed toward the inside carries means of arresting the motion of said tubular element, while co-operating with some means of abutment present on the internal wall of said tubular member; said tubular element maintains a continuity of fluid communication between said inflatable element and said means of supplying a fluid at a given pressure.

Further advantages and characteristics of this invention will result from the following description of certain embodiments of the same, offered for exemplifying and non-limiting purposes in reference to the attached drawings, in which:

BRIEF DESCRIPTION OF THE DRAWINGS

FIG. 1 is an elevational side view, with certain longitudinally sectional portions, of a first embodiment of the device of the invention;

FIG. 2 is a longitudinally sectional, enlarged view of a detail of the device shown in FIG. 1;

FIGS. 3 to 5 are elevational side views, partly sectional, illustrating the device's operation according to the invention;

FIG. 6 is an elevational side view of a second embodiment of the device of the invention;

FIG. 7 is an elevational side view of an enlarged detail of an alternative embodiment of the device according to the invention.

DESCRIPTION OF SOME PREFERRED EMBODIMENTS

Figure 3:
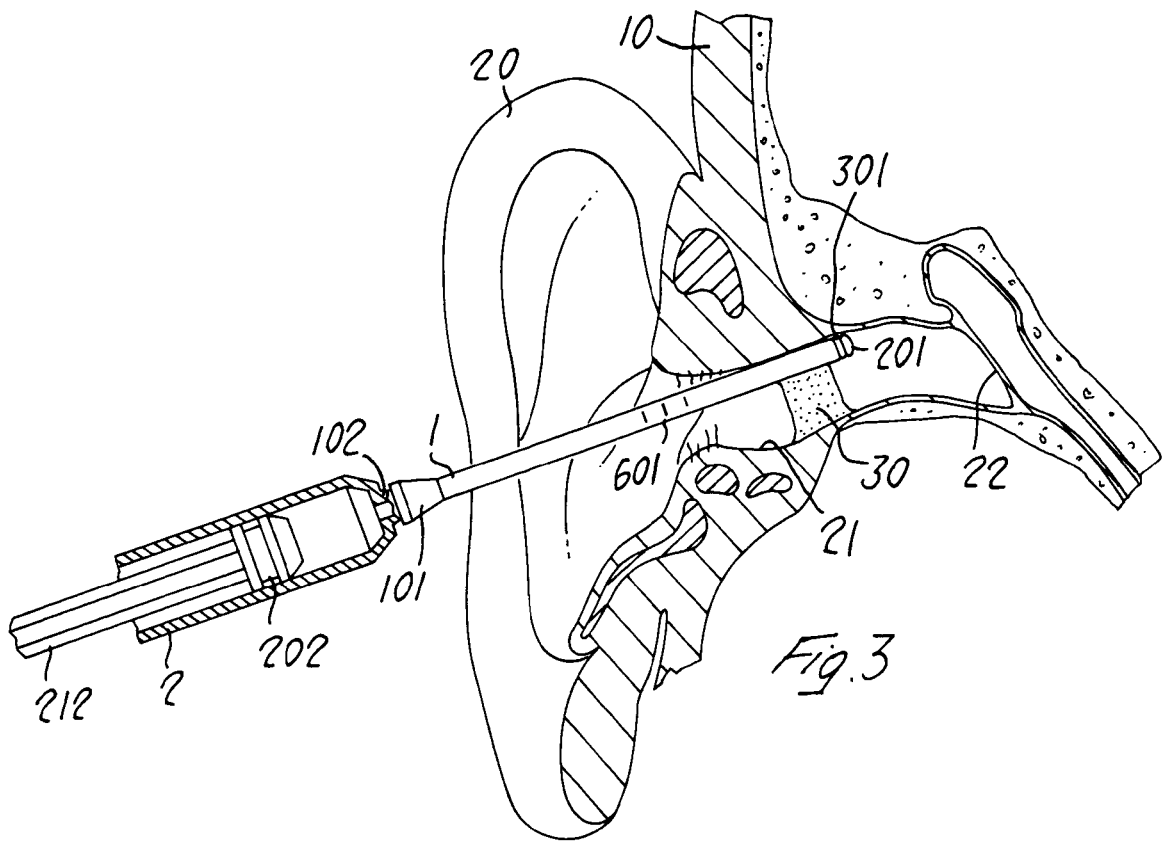

FIG. 1 illustrates a device according to this invention; 1 indicates the tubular member destined for insertion into the ear duct. This an member is fitted at one end with a spindle 101 engaging with the nozzle 102 of a syringe 2, and at the opposite end with an inflatable element 301, provided at its top with a rounded headpiece 201. The lateral wall of the tubular member is fitted with hollows 401, and reference notches 601 are also provided on the same. Inside the syringe 2, a piston 202 is arranged in a longitudinally mobile, fluid-tight manner, equipped with a rod 212 ending at its opposite end in a cap 232. The rod 212 carries flaps 222 projecting in a radial direction, which cooperate with the holes 312 and 302 formed in the walls of the syringe 2.

FIG. 2 illustrates the tubular member 1 in an enlarged longitudinal section; the same numbers fit the same parts. The inflatable element, the small balloon 301, is seen slipped over the tubular element 501, which is inserted into the tubular member 1 in a coaxial, longitudinally sliding manner; the mouthpiece 321 of the balloon 321 is permanently attached, for instance glued or thermally welded to the side wall of the element 501 for a certain stretch of its length, and exhibits at its end a swelling 311 that acts as a seal. At its end pointed toward the outside of the member 1, the tubular element 501 presents some radial apertures 511, while axially housing the holding bar 211 of the cap 201, which blocks the balloon 301 in between. The balloon is also shown, by a dotted and pointed line, in the configuration assumed after inflating, numbered 301'. The element 501 is at its opposite end fitted with the flaps 521 which are furnished with a toothed profile, capable of engaging with the corresponding contours produced by the hollows 401 formed on the sidewalls of the tubular member 1.

The operation of the device according to this invention will be evident from the following, with particular reference to the figures from 3 to 5 of the attached drawings. FIG. 3 illustrates a phase of introducing the device 1 into the ear 20 of a patient 10; the patient's ear duct 21 is obstructed by the accumulation of the waxy substance 30, and the device is introduced by sliding it along the walls of the ear duct, so that the cap 201 penetrates into the accumulation 30 and passes the same. The operator introducing the device 1 into the ear duct 21 controls the depth of the insertion by visually referring to the notches 601 present on the surface of the device. As shown in FIG. 3, the introduction is performed by sliding the device 1, or its end bearing the cap 201, along the wall of the ear duct 21. In this manner, the device should on one hand encounter less resistance upon introduction, and on the other hand minimise the risk of further compressing the occlusion 31 toward the ear drum membrane 22.

Figure 4:
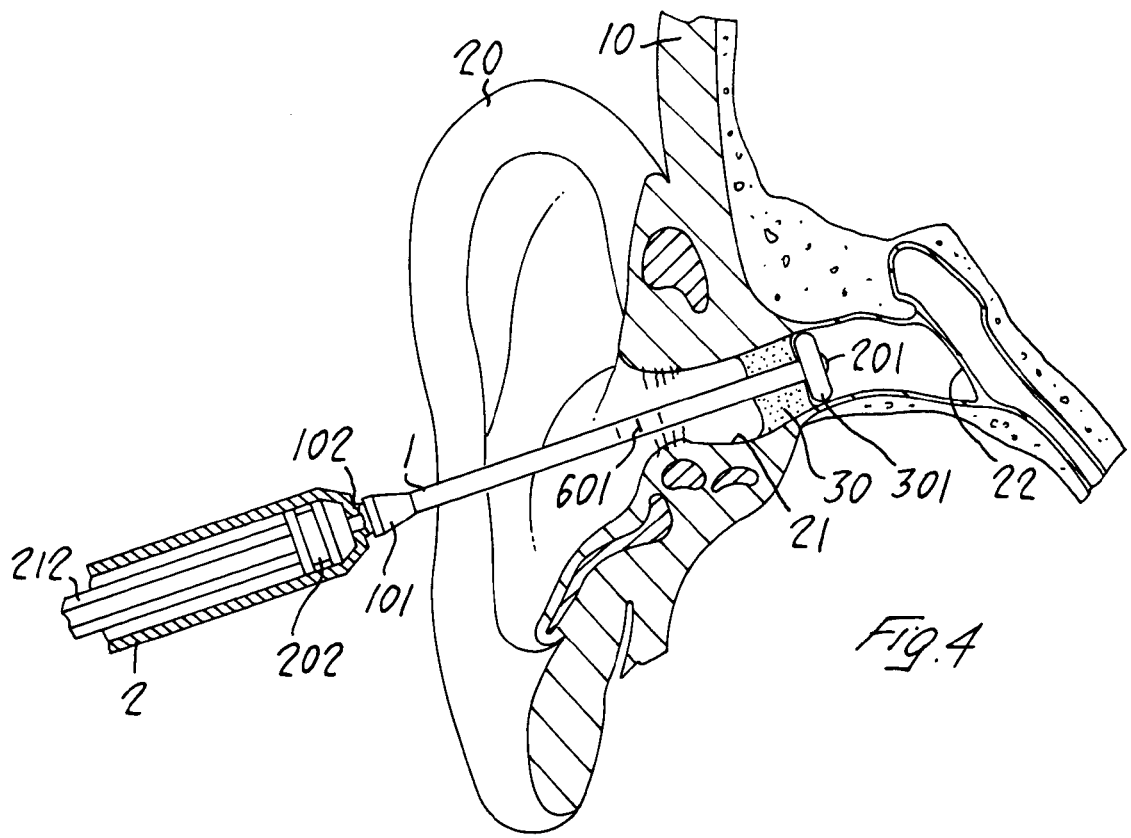

Once the end of the device 1 carrying the cap 201 has passed the occlusion 30, the operator may push on the rod 212 to actuate the piston 202 of the syringe 2, thereby achieving a transfer of the air contained in the syringe 2 toward the device 1. The balloon 301 inflates inside the ear duct 21, and the device positions itself as shown in FIG. 4, meaning that it self-centres with respect to the axis of the ear duct; it is precisely this capability of arranging itself at the centre of the ear duct 21, owing to the radial uniformity of the inflation of the balloon 301, that makes it advantageous to introduce the device along the walls of the ear duct itself. The volume of air introduced into the device 1 and therefore into the balloon 301 is regulated in advance, so that it cannot happen to become excessive and cause damage to the patient, on one hand, and will be effective for implementing the cleaning action of the ear duct, on the other hand. The balloon 301 will advantageously be properly lubricated, to avoid undesirable friction with the walls of the ear duct. The balloon 301 itself is shaped to adhere, once inflated, to the walls of the year duct 21, albeit without exercising a pressure on the walls themselves, or doing so to only a minimal degree.

The operator will subsequently extract the device from the ear duct 21 of the patient 10 while removing the occlusion 31, which will be dragged out by the action of the balloon 302. The device according to the invention allows cleaning the ear duct in an extremely accurate and safe manner, which minimises the risk of compressing the waxy material's occlusions toward the eardrum membrane, and facilitates the operator's task.

FIG. 6 illustrates an embodiment of the device of the invention; equal number fit equal parts. The tubular member 1 is connected by a spindle 101 to a hollow tubular body 3 carrying, at its end opposite that connected to the tubular member 1, a check valve coupled to an air supply conduit 104, which is in turn connected to a hand pump 4 equipped with a pressure gauge 204.

It is entirely evident that this embodiment's operation is absolutely analogous to that of the device previously pictured and described, except as regards the compressed air supply to the balloon 301, which is provided by the pump 4 through the body 3, while controlling the access pressure with the pressure gauge 204.

FIG. 7 illustrates an alternative embodiment of the device of the invention; the balloon 801, pictured here after inflating, presents some stiffening ribs 811 on its surface which boost the operating efficiency of cleaning the ear duct surfaces. The headpiece 701 also has a more pointed shape than the headpiece 202 shown above, and the helical contour 711 formed on the outer surface of said headpiece affords a better penetrating capacity of the same, at the moment of introducing it into the waxy occlusion.

Figure 8:
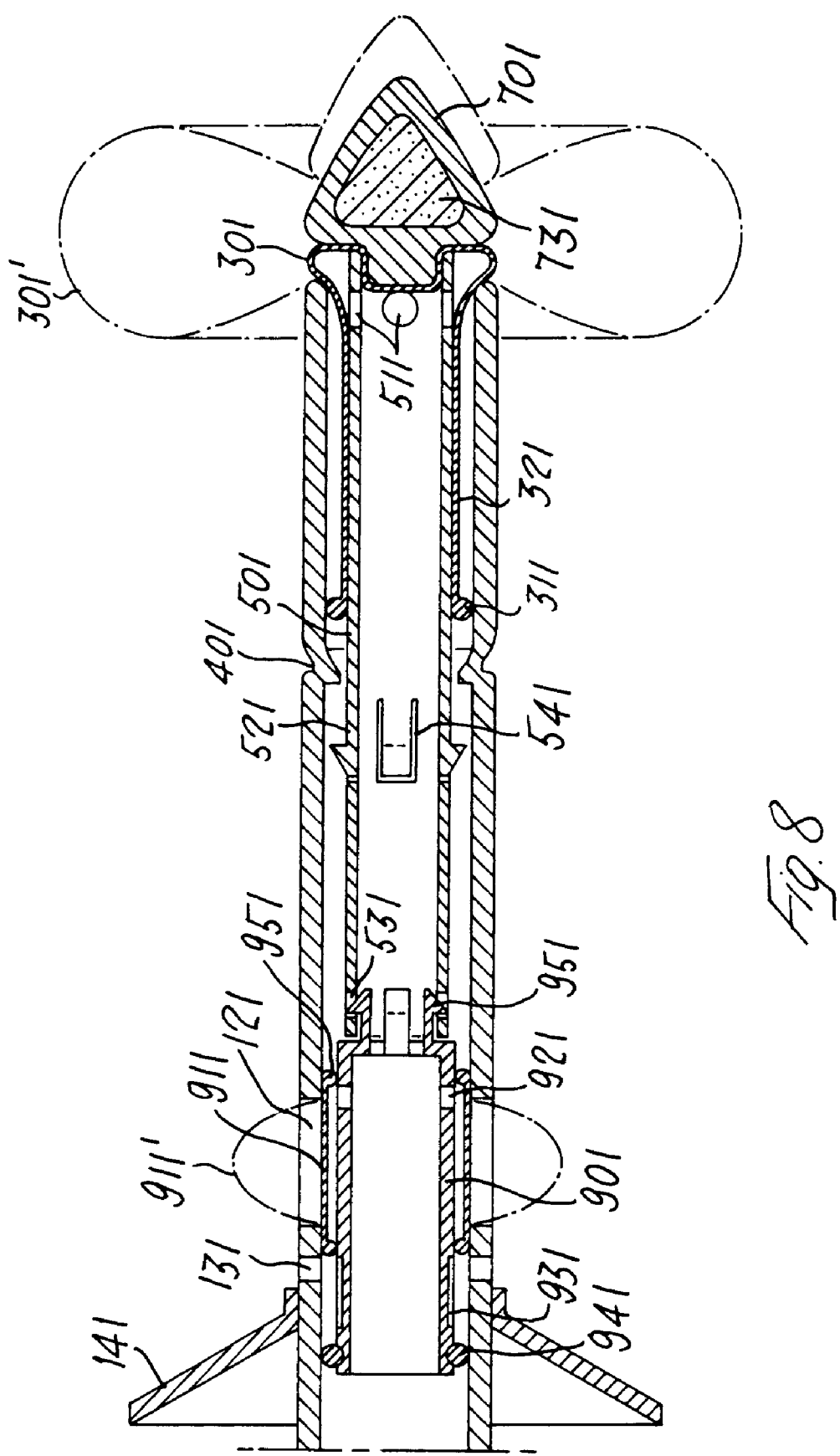
FIG. 8 is a sectional view of an enlarged detail of a third embodiment of the device of the invention.

FIG. 8 illustrates yet another embodiment of the device of the invention; equal numbers fit equal parts. The tubular element 501 extends in this case inside the member 1, well beyond the hollows 401 shaped in the same, and the flaps 521 are placed within some slots 541 formed in the lateral wall of said element 501. At the end fitting the balloon 301, the inserted holding bar 721 is relatively stiffer than the headpiece which is similar to that shown in FIG. 7; however, the headpiece 701 shown here in sectionalised form offers an internal fluid pocket 731, which may be filled with air or liquid, and is capable of better dampening the contact between the headpiece 701 and the ear duct.

At its opposite end, the element 501 exhibits a number of radial slots co-operating with the toothed flaps 951 of the sleeve 901, which is inserted into the member 1 in a sliding manner. Said member presents at least two ample radial apertures 121, while opposite these apertures, a layer of extensible material 911 is attached to its interior; the radial holes 131 are formed upstream of these apertures. The sleeve 901 is, at its end opposite to that connected to the tubular element 501, fitted with a sealing gasket 941; some longitudinal grooves 931 are carved into its outer surface, and the radial through holes 921 are formed next to the end connected to the element 501. A truncated conical collar 141 is also fitted over the member 1, upstream of the holes 131.

This additional embodiment offers two additional levels of user safety: a first pressure on the piston 202 of the syringe 2 results in inflating the extensible wall 911, as indicated by a pointed and dotted line numbered 911' in FIG. 8. The air crosses the holes 921 of the sleeve 901, while the rims 951 of the extensible wall guarantee a sealing action. The wall 911 extending through the apertures 121 limits the stroke of the member 1 inside the ear duct, thus enhancing the operator's control upon introducing the device. The further inflow of air into the member 1 tends to inflate the balloon 301, and to consequently shift the tubular element 501 in the direction of the balloon 301 itself. The latter drags along the sleeve 901 it is coupled to, and the grooves 931 shaped into the wall of the sleeve are therefore moved into the chamber bounded by the extensible wall 911. The wall 911 will consequently gradually deflate, thus allowing a further portion of the member 1 to be introduced into the ear duct. When the holes 921 have exceeded the rims 951 of the extensible walls, any losses of air pressure will no longer be possible, and the injected air will inflate the balloon 301. The headpiece 701 is advantageously built in a manner to hold a fluid pocket 731 in its interior, in order to better soften the contact between the headpiece 701 itself and the ear duct. The frustoconical-shaped collar 141 finally prevents a further accidental introduction of the member 1 into the ear duct.

I claim:

1. An ear duct cleaning device, comprising:
    a flexible tubular member equipped at one end with an inflatable element and at its opposite end with means of supplying a fluid at a certain pressure, where said inflatable element is coupled to means of controlling the inflation in a manner so that said inflatable element assumes, once inflated, a shape such that its radial extension with respect to the axis of said tubular member is considerably greater than that along the same axis,
    said means of controlling the inflation of said inflatable element comprising means of limiting the extension of said inflatable element in the direction of the axis of said tubular member, and
    said means of limiting the extension of said inflatable element in the direction of the axis of said tubular member comprises a tubular element, said inflatable element is slipped over, while sliding longitudinally in a sealed manner inside said tubular member, coaxially and concentrically to the same, wherein an end toward the outside of said tubular element carries means of blocking said inflatable element, while means are provided on the lateral wall of said tubular element for arresting the motion of the same, which are placed at a given distance from the end of the tubular element that said inflatable element is fitted upon, and are co-operating with the means of blocking present on the internal wall of said tubular member, wherein said tubular element maintains a continuity of fluid communication between said inflatable element and said means of supplying fluid at a given pressure.

2. The device according to claim 1, wherein on said flexible tubular member, means are provided for controlling the introduction of said member into the ear duct.

3. The device according to claim 2, wherein said means of controlling the introduction comprises a portion of an extensible wall arranged opposite a plurality of radial apertures appropriately positioned on said member, where said extensible wall forms a swelling protruding in a radial direction from said member at a first admission of fluid, and where said swelling subsequently retracts for a further admission of fluid.

4. The device according to claim 1, wherein said means of blocking said inflatable element on the end of said tubular element comprises a headpiece equipped with a holding bar capable of inserting itself into said tubular element, thus holding said inflatable element in between.

5. The device according to claim 4, wherein said headpiece is substantially rounded.

6. The device according to claim 4, wherein said headpiece is substantially built in the form of an elliptical cover.

7. The device according to claim 6, wherein said headpiece exhibits one or more helical contours on its lateral outer surface.

8. The device according to claim 4, wherein said headpiece is equipped with an internal pocket capable of containing a fluid.

9. The device according to claim 1, wherein a mouthpiece of said inflatable element is fitted with a swelling capable of guaranteeing a sealed sliding motion of a tubular element inside said tubular member.

10. The device according to claim 1, wherein the said means of supplying a fluid at a certain pressure comprise syringe type means.

11. The device according to claim 10, wherein said syringe type means are equipped with means capable of preventing the extraction of a stem of a piston of said syringe.

12. The device according to claims 10, wherein said syringe-type means are fitted with means capable of preventing the removal of a piston from its position at an end of a run.

13. The device according to claim 1, wherein said means of supplying a fluid at a certain pressure comprise pumping means fitted with a pressure gauge connected to said tubular member by a conduit and operating means, while a check valve is being provided.

14. The device according to claim 1, wherein said flexible tubular member carries, on its outer wall, a plurality of reference markings on its position, at convenient intervals from each other.

15. The device according to claim 1, where said inflatable element is appropriately lubricated.

16. The device according to claim 1, wherein said inflatable element is formed so that when fully inflated, it adheres to the walls of the ear duct, without any or with only a minimal pressure on the same.

17. The device according to claim 1, wherein said inflatable element is fitted on its outer surface with a plurality of reinforcing ribs.

18. A method for using an ear duct cleaning device, comprising:

a flexible tubular member equipped at one end with an inflatable element and at its opposite end with means of supplying a fluid at a certain pressure, where said inflatable element is coupled to means of controlling the inflation in a manner so that said inflatable element assumes, once inflated, a shape such that its radial extension with respect to the axis of said tubular member is considerably greater than that along the same axis, said means of controlling the inflation of said inflatable element comprising means of limiting the extension of said inflatable element in the direction of the axis of said tubular member, and said means of limiting the extension of said inflatable element in the direction of the axis of said tubular member comprises a tubular element, said inflatable element is slipped over, while sliding longitudinally in a sealed manner inside said tubular member, coaxially and concentrically to the same, wherein an end toward the outside of said tubular element carries means of blocking said inflatable element, while means are provided on the lateral wall of said tubular element for arresting the motion of the same, which are placed at a given distance from the end of the tubular element that said inflatable element is fitted upon, and are co-operating with the means of blocking present on the internal wall of said tubular member, wherein said tubular element maintains a continuity of fluid communication between said inflatable element and said means of supplying fluid at a given pressure, said method comprising:

introducing the inflatable element along the wall of the ear duct of the patient;

inflating said inflatable element by means capable of supplying a fluid at a certain pressure; and extracting said tubular member from said ear duct.

* * * * *